(12) United States Patent
Charlton et al.

(10) Patent No.: US 8,978,026 B2
(45) Date of Patent: Mar. 10, 2015

(54) ARCHITECTURE FOR FIELD UPGRADE OF A HEALTH MONITORING SYSTEM

(75) Inventors: Steven Charlton, Osceola, IN (US); Jun Chen, Warren, NJ (US); Lin Chen, Hopewell Jct., NY (US); Qiang Fu, Briarcliff Manor, NY (US); Igor Gofman, Croton-on-Hudson, NY (US); Steven B. Harris, Briarcliff Manor, NY (US); Paul L. Inman, Nyack, NY (US); Gary J. Johnson, Lagrangeville, NY (US); Qiong Li, Tappan, NY (US); Harris Lieber, White Plains, NY (US); Derek Lok, Mohegan Lake, NY (US); Tony Nguyen, Valhalla, NY (US); Paul M. Ripley, Nanuet, NY (US); Gregory Stefkovic, Mahopac, NY (US); Hoi-Cheong Steve Sun, Mount Kisco, NY (US)

(73) Assignee: Bayer HealthCare LLC, Whippany, NJ (US)

( * ) Notice: Subject to any disclaimer, the term of this patent is extended or adjusted under 35 U.S.C. 154(b) by 1896 days.

(21) Appl. No.: 12/129,570

(22) Filed: May 29, 2008

(65) Prior Publication Data

US 2008/0301665 A1 Dec. 4, 2008

Related U.S. Application Data

(60) Provisional application No. 60/932,286, filed on May 30, 2007, provisional application No. 61/012,721, filed on Dec. 10, 2007, provisional application No. 61/012,718, filed on Dec. 10, 2007.

(51) Int. Cl.
*G06F 9/44* (2006.01)
*A61B 5/145* (2006.01)
(Continued)

(52) U.S. Cl.
CPC .............. *A61B 5/14532* (2013.01); *G06F 8/65* (2013.01); *G06Q 50/22* (2013.01); *G06F 1/16* (2013.01); *G06F 19/3406* (2013.01); *H04L 29/08072* (2013.01); *G06F 8/61* (2013.01)
USPC ........... 717/173; 717/172; 717/171; 717/178; 717/177; 705/2; 705/3; 709/217; 709/219

(58) Field of Classification Search
USPC .................................................. 717/168–718
See application file for complete search history.

(56) References Cited

U.S. PATENT DOCUMENTS

| | | | |
|---|---|---|---|
| 5,307,263 | A | 4/1994 | Brown |
| 5,379,214 | A | 1/1995 | Arbuckle |

(Continued)

FOREIGN PATENT DOCUMENTS

| | | |
|---|---|---|
| CN | 1525318 | 9/2004 |
| EP | 1099114 | 6/1999 |

(Continued)

OTHER PUBLICATIONS

Brooks, R., "Mobile Code Paradigms and Security Issues", IEEE Internet Computing, IEEE Service Center, New York, NY, vol. 8, No. 3, May 1, 2004, pp. 54-59, XP011112882, ISSN: 1089-7801.

(Continued)

*Primary Examiner* — Lewis A Bullock, Jr.
*Assistant Examiner* — Tina Huynh
(74) *Attorney, Agent, or Firm* — Nixon Peabody LLP

(57) ABSTRACT

An architecture allows individual system components to be developed and tested individually, i.e., as distinct modules, and to be subsequently combined through standardized electrical and communication interfaces. Any combination of these modules can be implemented to form different products that provide any number of functions, such as an integrated system for monitoring a health condition and/or delivering a medication. The architecture also provides an approach for dynamically updating the product and offering its users the latest generation of technology even after the users have already purchased the product. In particular, the embodiments employ the communication interfaces to also provide connection to a remote network that can update or upgrade the product's software when the product is out in the field.

17 Claims, 11 Drawing Sheets

(51) Int. Cl.
*G06F 9/445* (2006.01)
*G06Q 50/22* (2012.01)
*G06F 1/16* (2006.01)
*G06F 19/00* (2011.01)
*H04L 29/08* (2006.01)

(56) References Cited

U.S. PATENT DOCUMENTS

| | | | |
|---|---|---|---|
| 5,704,366 A | 1/1998 | Tacklind et al. | |
| 5,899,855 A | 5/1999 | Brown | |
| 6,134,504 A | 10/2000 | Douglas et al. | |
| 6,144,922 A | 11/2000 | Douglas et al. | |
| 6,347,396 B1 | 2/2002 | Gard et al. | |
| 6,558,320 B1 | 5/2003 | Causey, III et al. | |
| 6,575,900 B1 | 6/2003 | Zweig et al. | |
| 6,602,191 B2 | 8/2003 | Quy | |
| 6,641,533 B2 | 11/2003 | Causey, III et al. | |
| 6,728,787 B1 | 4/2004 | Leigh | |
| 6,735,551 B2 | 5/2004 | Voegeli et al. | |
| 6,768,425 B2 | 7/2004 | Flaherty et al. | |
| 6,836,657 B2* | 12/2004 | Ji et al. | 455/419 |
| 6,891,936 B2 | 5/2005 | Kai et al. | |
| 6,959,247 B2 | 10/2005 | Neel et al. | |
| 6,976,958 B2 | 12/2005 | Quy | |
| 7,028,114 B1 | 4/2006 | Milan et al. | |
| 7,041,468 B2 | 5/2006 | Drucker et al. | |
| 7,051,157 B2 | 5/2006 | James | |
| 7,060,031 B2 | 6/2006 | Webb et al. | |
| 7,103,578 B2 | 9/2006 | Beck et al. | |
| 7,156,808 B2 | 1/2007 | Quy | |
| 7,156,809 B2 | 1/2007 | Quy | |
| 7,165,109 B2 | 1/2007 | Chiloyan et al. | |
| 7,181,731 B2 | 2/2007 | Pace et al. | |
| 7,286,894 B1 | 10/2007 | Grant et al. | |
| 7,344,500 B2 | 3/2008 | Talbot et al. | |
| 7,436,311 B2 | 10/2008 | Rapaport et al. | |
| 7,447,643 B1 | 11/2008 | Olson et al. | |
| 7,467,065 B2 | 12/2008 | Neel et al. | |
| 7,738,264 B2 | 6/2010 | Christol et al. | |
| 2001/0044588 A1 | 11/2001 | Mault | |
| 2002/0193679 A1 | 12/2002 | Malave et al. | |
| 2003/0032077 A1 | 2/2003 | Itoh et al. | |
| 2003/0036683 A1 | 2/2003 | Kehr et al. | |
| 2003/0110346 A1* | 6/2003 | Katahira | 711/103 |
| 2003/0188303 A1* | 10/2003 | Barman et al. | 717/170 |
| 2004/0015952 A1* | 1/2004 | Lajoie et al. | 717/171 |
| 2004/0038389 A1* | 2/2004 | Maus et al. | 435/287.2 |
| 2004/0073095 A1 | 4/2004 | Causey, III et al. | |
| 2004/0147969 A1 | 7/2004 | Mann et al. | |
| 2004/0176913 A1 | 9/2004 | Kawatahara et al. | |
| 2004/0186746 A1 | 9/2004 | Angst et al. | |
| 2004/0193998 A1* | 9/2004 | Blackburn et al. | 714/763 |
| 2004/0243992 A1* | 12/2004 | Gustafson et al. | 717/168 |
| 2004/0249999 A1 | 12/2004 | Connolly et al. | |
| 2005/0003470 A1 | 1/2005 | Nelson et al. | |
| 2005/0113650 A1 | 5/2005 | Pacione et al. | |
| 2005/0132351 A1* | 6/2005 | Randall et al. | 717/168 |
| 2005/0223374 A1* | 10/2005 | Wishart et al. | 717/173 |
| 2005/0239156 A1 | 10/2005 | Drucker et al. | |
| 2005/0267780 A1 | 12/2005 | Ray et al. | |
| 2005/0276092 A1 | 12/2005 | Hansen et al. | |
| 2005/0277164 A1 | 12/2005 | Drucker et al. | |
| 2006/0009684 A1 | 1/2006 | Kim | |
| 2006/0010098 A1 | 1/2006 | Goodnow et al. | |
| 2006/0015861 A1* | 1/2006 | Takata et al. | 717/168 |
| 2006/0026304 A1* | 2/2006 | Price | 710/8 |
| 2006/0232287 A1 | 10/2006 | Stemer et al. | |
| 2006/0248398 A1 | 11/2006 | Neel et al. | |
| 2007/0004969 A1 | 1/2007 | Kong et al. | |
| 2007/0033074 A1 | 2/2007 | Nitzan et al. | |
| 2007/0040449 A1 | 2/2007 | Spurlin et al. | |
| 2007/0055799 A1 | 3/2007 | Koehler et al. | |
| 2007/0061393 A1 | 3/2007 | Moore | |
| 2007/0088521 A1* | 4/2007 | Shmueli et al. | 702/127 |
| 2007/0152683 A1 | 7/2007 | Werner et al. | |
| 2007/0152812 A1* | 7/2007 | Wong et al. | 340/539.12 |
| 2007/0156033 A1 | 7/2007 | Causey, III et al. | |
| 2007/0169075 A1* | 7/2007 | Lill et al. | 717/168 |
| 2007/0174467 A1 | 7/2007 | Ballou et al. | |
| 2007/0177426 A1 | 8/2007 | Dellacona | |
| 2007/0179352 A1 | 8/2007 | Randlov et al. | |
| 2007/0185545 A1 | 8/2007 | Duke | |
| 2007/0198995 A1 | 8/2007 | Dellacona | |
| 2007/0213608 A1 | 9/2007 | Brown | |
| 2007/0231846 A1 | 10/2007 | Cosentino et al. | |
| 2007/0233395 A1 | 10/2007 | Neel et al. | |
| 2007/0253380 A1 | 11/2007 | Jollota et al. | |
| 2007/0255348 A1 | 11/2007 | Holtzclaw | |
| 2007/0258395 A1 | 11/2007 | Jollota et al. | |
| 2007/0273504 A1 | 11/2007 | Tran | |
| 2007/0276197 A1 | 11/2007 | Harmon | |
| 2007/0276270 A1* | 11/2007 | Tran | 600/508 |
| 2008/0015422 A1 | 1/2008 | Wessel | |
| 2008/0040449 A1 | 2/2008 | Grant et al. | |
| 2008/0097551 A1 | 4/2008 | Dicks et al. | |
| 2008/0097910 A1 | 4/2008 | Dicks et al. | |
| 2008/0097911 A1 | 4/2008 | Dicks et al. | |
| 2008/0103554 A1 | 5/2008 | Dicks et al. | |
| 2008/0168188 A1 | 7/2008 | Yue et al. | |
| 2008/0215360 A1 | 9/2008 | Dicks et al. | |
| 2008/0234943 A1 | 9/2008 | Ray et al. | |
| 2008/0234992 A1 | 9/2008 | Ray et al. | |
| 2008/0235053 A1 | 9/2008 | Ray et al. | |
| 2008/0262329 A1 | 10/2008 | Say et al. | |
| 2008/0288180 A1 | 11/2008 | Hayter et al. | |
| 2008/0294024 A1* | 11/2008 | Cosentino et al. | 600/309 |
| 2008/0300919 A1 | 12/2008 | Charlton et al. | |
| 2008/0301665 A1* | 12/2008 | Charlton et al. | 717/170 |
| 2008/0301668 A1* | 12/2008 | Zachmann | 717/173 |
| 2008/0319295 A1 | 12/2008 | Bernstein | |
| 2009/0030382 A1 | 1/2009 | Brandt | |
| 2009/0099864 A1* | 4/2009 | Cronrath et al. | 705/2 |
| 2009/0158274 A1* | 6/2009 | Roberts | 717/178 |
| 2009/0304547 A1 | 12/2009 | Werner et al. | |
| 2010/0146300 A1* | 6/2010 | Brown | 713/189 |
| 2010/0228111 A1* | 9/2010 | Friman et al. | 600/365 |

FOREIGN PATENT DOCUMENTS

| | | |
|---|---|---|
| EP | 1460516 | 7/1999 |
| EP | 1559364 | 8/2002 |
| EP | 1722310 | 4/2005 |
| EP | 1611839 | 6/2005 |
| EP | 1850226 | 4/2007 |
| WO | WO 00/05581 | 6/1999 |
| WO | WO 02/094092 | 4/2002 |

OTHER PUBLICATIONS

International Search Report corresponding to International Patent Application No. PCT/US2008/006814, dated Oct. 1, 2008, 4 pages.
Written Opinion corresponding to International Patent Application No. PCT/US2008/006814, dated Oct. 1, 2008, 8 pages.
Office Action corresponding to U.S. Appl. No. 12/129,555, dated Jun. 21, 2011, 12 pages.

* cited by examiner

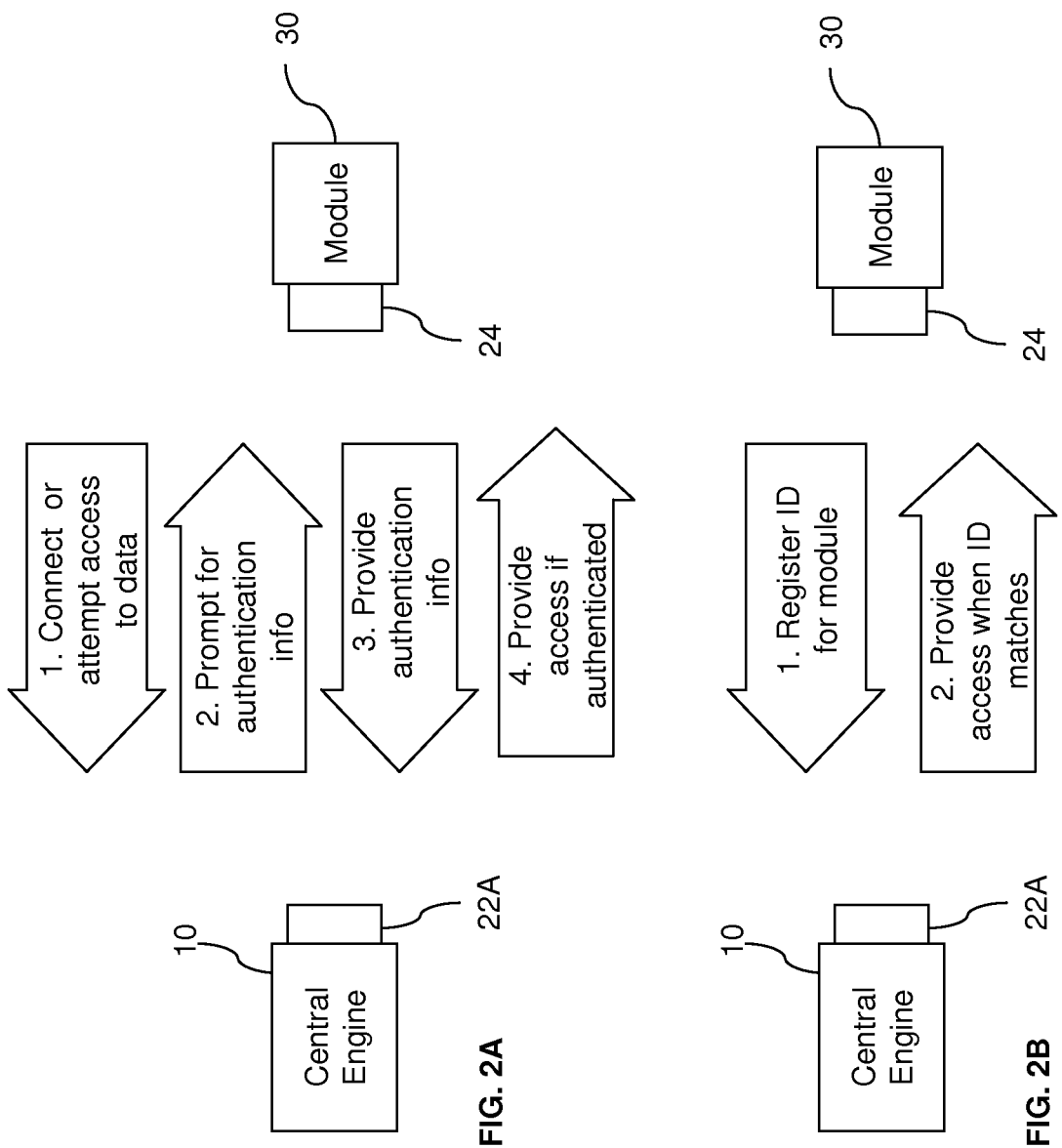

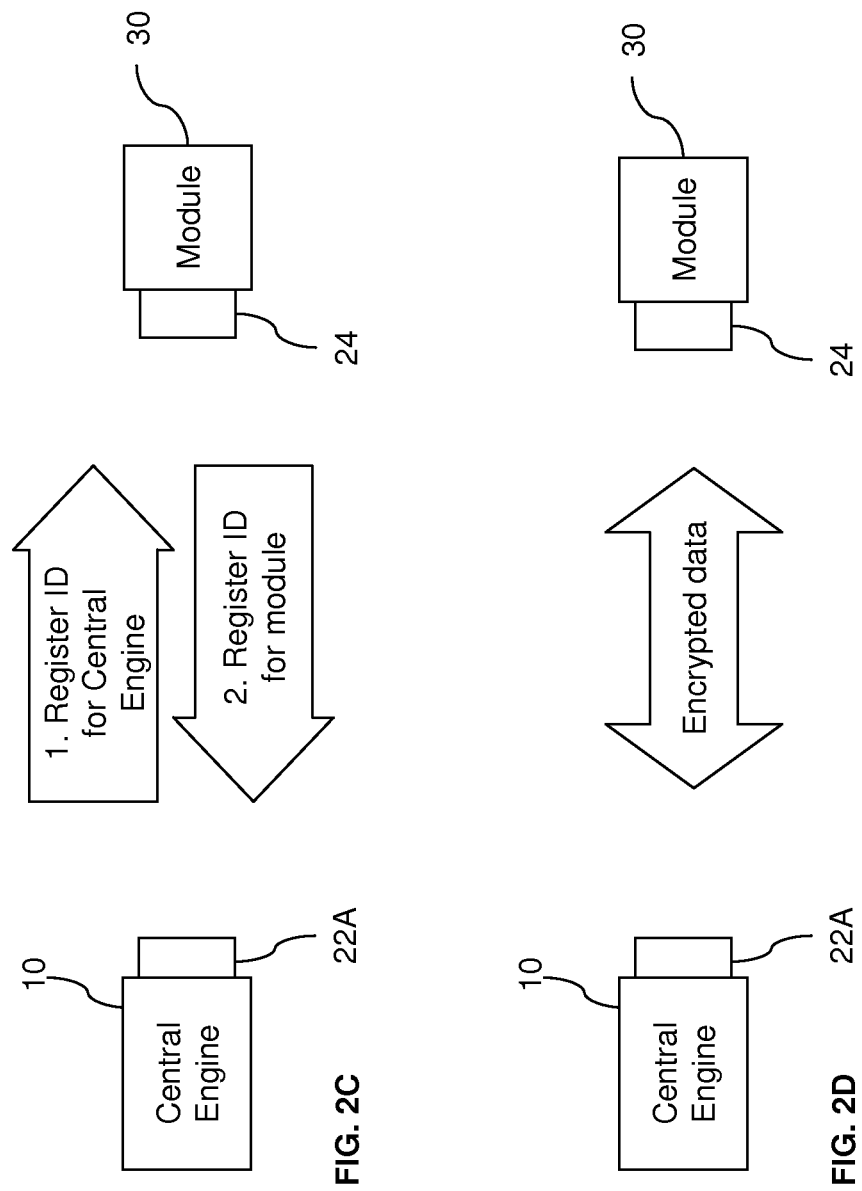

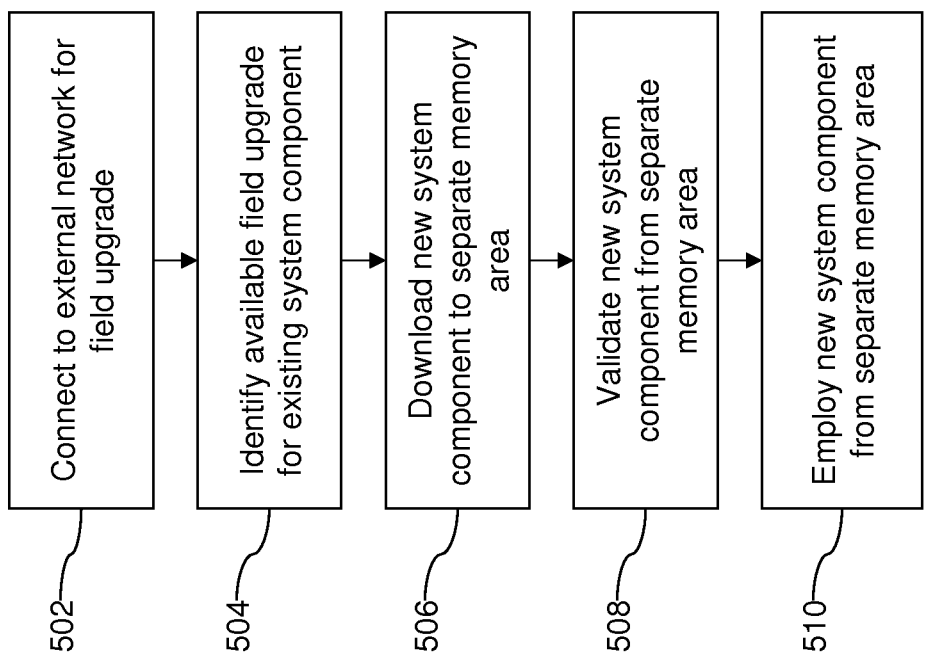

ARCHITECTURE FOR FIELD UPGRADE OF A HEALTH MONITORING SYSTEM

CROSS REFERENCE TO RELATED APPLICATIONS

This application claims priority to U.S. Provisional Application No. 60/932,286, filed May 30, 2007, U.S. Provisional Application No. 61/012,721, filed Dec. 10, 2007, and U.S. Provisional No. 61/012,718, filed Dec. 10, 2007, the contents of which are incorporated entirely herein by reference.

FIELD OF THE INVENTION

The present invention relates generally to a method and system for developing healthcare devices. More specifically, the method and system of the present invention provides an architecture that allows any combination of modules with different functions to be easily assembled to form an integrated system for monitoring a health condition and/or delivering a medication. In addition, the method and system provides an architecture that allows the modules to be updated dynamically during operation in the field.

BACKGROUND OF THE INVENTION

The quantitative determination of analytes in body fluids is of great importance in the diagnoses and maintenance of certain physiological conditions. For example, individuals with diabetes frequently check the glucose level in their bodily fluids. The results of such tests can be used to regulate the glucose intake in their diets and/or to determine whether insulin or other medication needs to be administered.

Diagnostic systems, such as blood-glucose systems, may employ a meter or instrument to calculate the glucose value in a blood sample from an individual. Such instruments operate by measuring an output, such as current or color, from a reaction with the glucose in the sample. The test results typically are displayed and stored by the meter. Basic systems allow the user to access the test results directly from the meter via a keypad or other interactive component.

Other diagnostic systems, however, provide more advanced functionality to allow a user to process and manage test results. For example, some systems allow a user to load test results from a blood-glucose meter onto a processing device, such as a conventional desktop personal computer (PC), and to process and display the results with a data-management application. However, using the processing power of PC technology to organize results from a blood-glucose meter is just one example of how diagnostic systems provide more functionality by incorporating different technologies into a diagnostic process.

Although integrating different technologies and functions may yield highly sophisticated and extremely useful diagnostic systems, the introduction of such systems into the marketplace is slowed by current approaches to product design and development in the industry. For example, current approaches to the design of multi-function products employ complicated system architectures that interconnect the variety of functional elements via distinct and non-standard techniques. Accordingly, a functional element must be developed with the specific final product and the other functional elements in mind. In other words, the complex architecture results in dependencies between functional elements, and thus does not allow each element to be developed independently and/or in parallel. As such, the development process requires more time as more components are added and complexity is increased.

In addition, although the final integrated product may provide the features and advantages of a variety of technologies, the rapid pace of change in these technologies may outdate the final product before the final product is introduced to the market, particularly because product development takes such a long time. In other words, current approaches to product development make it difficult to ensure that the users of the product have the latest generation of technology. Where the cost of integrated products may be relatively high due to the greater amount of functionality, consumers may find less justification in purchasing such products when their technology may become quickly outdated.

In view of the foregoing, there is a need for design and development approaches that simplify the process of combining different technological components into a single product while meeting the high quality standards for medical devices. In particular, there is a need for an approach that simplifies interfaces between components and therefore permits different combinations of components to be easily and reliably integrated regardless of the number of components. Moreover, there is a need for an approach that allows the final product to be dynamically and continuously updated to offer its users the most current technology.

SUMMARY OF THE INVENTION

The embodiments described herein address the needs identified above by providing an architecture that allows individual system components to be developed and tested individually, i.e., as distinct modules, and to be subsequently combined through standardized electrical and communication interfaces. Any combination of these modules can be implemented to form different products that provide any number of functions, such as an integrated system for monitoring a health condition and/or delivering a medication.

Although the architecture makes it more feasible to shorten a product's development cycle and to introduce the product to consumers more quickly, the embodiments also provide an approach for dynamically updating the product and offering its users the latest generation of technology even after the users have already purchased the product. In particular, the embodiments employ the communication interfaces to also provide connection to a remote network that can update or upgrade the product's software when the product is out in the field. This process is known as a field upgrade.

Because the interfaces and communication protocols are designed to facilitate connection between different components and the rest of the system, the embodiments also provide functionality that ensures that unauthorized individuals or devices cannot connect with the system and compromise the security of data, such as personal medical information, which may be collected, stored, and handled by the system. With this underlying security functionality, particular technologies, such as wireless communication, can be implemented as components of medical diagnostic systems without concern over unauthorized access to personal information.

In addition, due to the important medical functions associated with the assembled product, embodiments employ validation procedures to ensure that any data transferred to the product, for example, during field upgrade, does not corrupt the data or the software stored by the product and that the product continues to operate as expected.

Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive. The invention is to cover all modifications, equivalents, and alternatives falling within the spirit and scope of the invention.

BRIEF DESCRIPTION OF THE DRAWINGS

FIG. 2A illustrates an example security measure that can be employed by an architecture according to aspects of the present invention.

FIG. 2B illustrates another example security measure that can be employed by an architecture according to aspects of the present invention.

FIG. 2C illustrates a further example security measure that can be employed by an architecture according to aspects of the present invention.

FIG. 2D illustrates yet another example security measure that can be employed by an architecture according to aspects of the present invention.

FIG. 9 illustrates an example for employing a field upgrade according to aspects of the present invention.

DESCRIPTION OF ILLUSTRATED EMBODIMENTS

The embodiments described herein provide a system architecture that allows individual system components, or modules, to be developed and validated independently (as distinct modules) and subsequently combined through standardized electrical and communication interfaces. The standardized interfaces facilitate the combination and configuration of these modules to form different products that provide any number of functions. While the architecture can be used to form a fixed combination of components, the approach also permits reconfigurable or expandable combinations where different components may be easily removed or added to the system. In addition, as described further below, the architecture provides an approach for dynamically updating the modules after they have been integrated into the product.

Figure 1A:
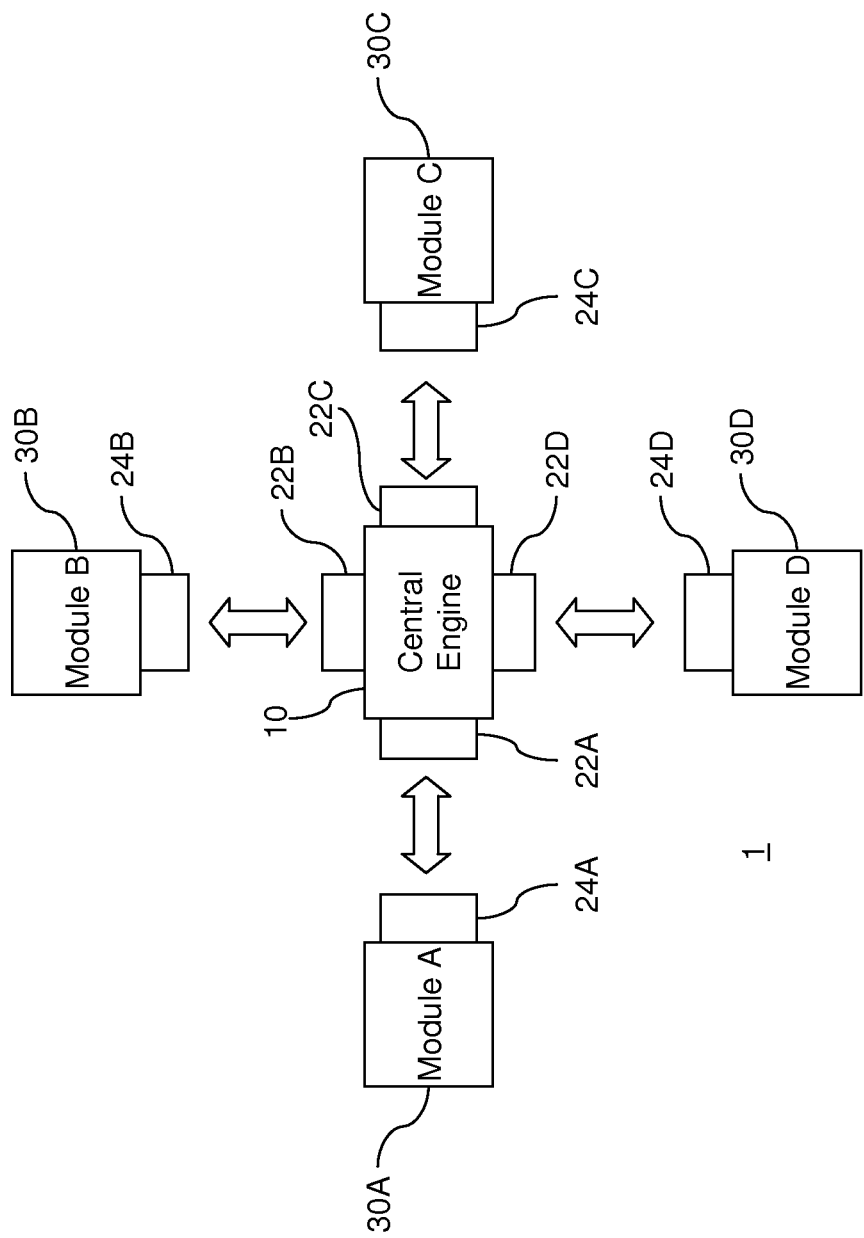
FIG. 1A illustrates a diagram of an architecture according to aspects of the present invention.

FIG. 1A illustrates a conceptual diagram of a modular architecture according to aspects of the present invention. As shown in FIG. 1A, a modular architecture system 1 includes central engine 10 that is connected to a plurality of modules 30A, 30B, 30C, and 30D, each of which provides a functionality for a health monitoring and delivery system. The central engine 10 enables the modules 30A, 30B, 30C, and 30D to work as an effective system. For example, the central engine 10 allows information to be communicated between the modules 30A, 30B, 30C, and 30D. For example, module 30D may be a computing device with software that processes data received from the other modules 30A, 30B, and 30C via the central engine 10. As FIG. 1A further illustrates, interface elements 22A, 22B, 22C, and 22D of the central engine 10 connect with respective interface elements 24A, 24B, 24C, and 24D to establish communications between the central engine 10 and the modules 30A, 30B, 30C, and 30D. The interfaces may provide wired, i.e. physical, and/or wireless communications. Advantageously, the centralized organization of the interface architecture facilitates the integration of modules 30A, 30B, 30C, and 30D, which can be developed and tested separately from each other. Moreover, although the interface elements 22A, 22B, 22C, and 22D of the central engine 10 do not have to follow the same communications protocol, the interface elements 22A, 22B, 22C, and 22D can employ the most widely-used standard protocols so that the central engine 10 is more likely to be compatible with a given module.

Although the modules 30A, 30B, 30C, and 30D of FIG. 1A may all communicate information with each other, it is contemplated that a module connected to the central engine 10 does not have to communicate with all of the other modules. Indeed, a module may be communicatively isolated from any, including all, of the other modules. For example, the nature of data and/or software on a particular module may be highly sensitive, so the module may be isolated from the other modules to enhance the security and/or integrity of the data.

In one embodiment, the central engine 10 is implemented on a mother board, while each module is separately implemented on a daughter board. The daughter boards are standardized so that they may connect to a single mother board to be integrated with the system. In other words, specific interfaces with boards corresponding to other modules do not have to be developed each time a new module is implemented. Due to this standardized approach, using commercial off-the-shelf (COTS) hardware for the mother and daughter boards becomes more feasible. Advantageously, using COTS hardware requires less development time than an application-specific integrated circuit (ASIC) approach.

In some embodiments, the mother board and the daughter boards may physically reside on separate circuit boards. In other embodiments, the mother board and the daughter boards may all be physically integrated onto the same circuit board. In further embodiments, the mother board and a combination of daughter boards may be physically integrated onto the same circuit board, while other daughter boards reside on separate circuit boards. Moreover, in some embodiments, the mother board and the daughter boards, whether on the same circuit boards or not, may all be disposed in the same housing, or casing. Meanwhile, in other embodiments, some or all of the daughter boards may be disposed in one or more housings separate from the mother board's housing. In general, the components of embodiments may be subject to varying degrees of physical integration regarding assembly on different circuit boards or within different housings, etc. To accommodate this variation in physical configuration, more than one interface type may be required to connect the daughter boards to the mother board, but as discussed previously, the interfaces between the central engine and the modules do not have to follow the same communications protocol. The interface elements associated with the mother board can employ the most widely-used standard protocols so that the central engine is more likely to be compatible with a given module.

The centralized architecture using standardized interfaces facilitates the development of compatible modules. When adding functionality to the system, integration with the architecture is easily achieved by employing a compatible interface element. Moreover, the new module can be developed independently of the other modules, because only a single interface with the central engine 10 is required. In other words, even if the new module must communicate with other modules in the system, the new module does not have to be designed for a direct connection with the other modules, so the communications configuration of the other modules is not a significant design consideration for the new module. Accordingly, the ability to independently develop additional modules that easily connect with the central engine 10 enables systems employing this architecture to be flexible and reconfigurable. For example, such a system can be expanded with new modules or upgraded with new versions of existing modules.

Figure 1B:
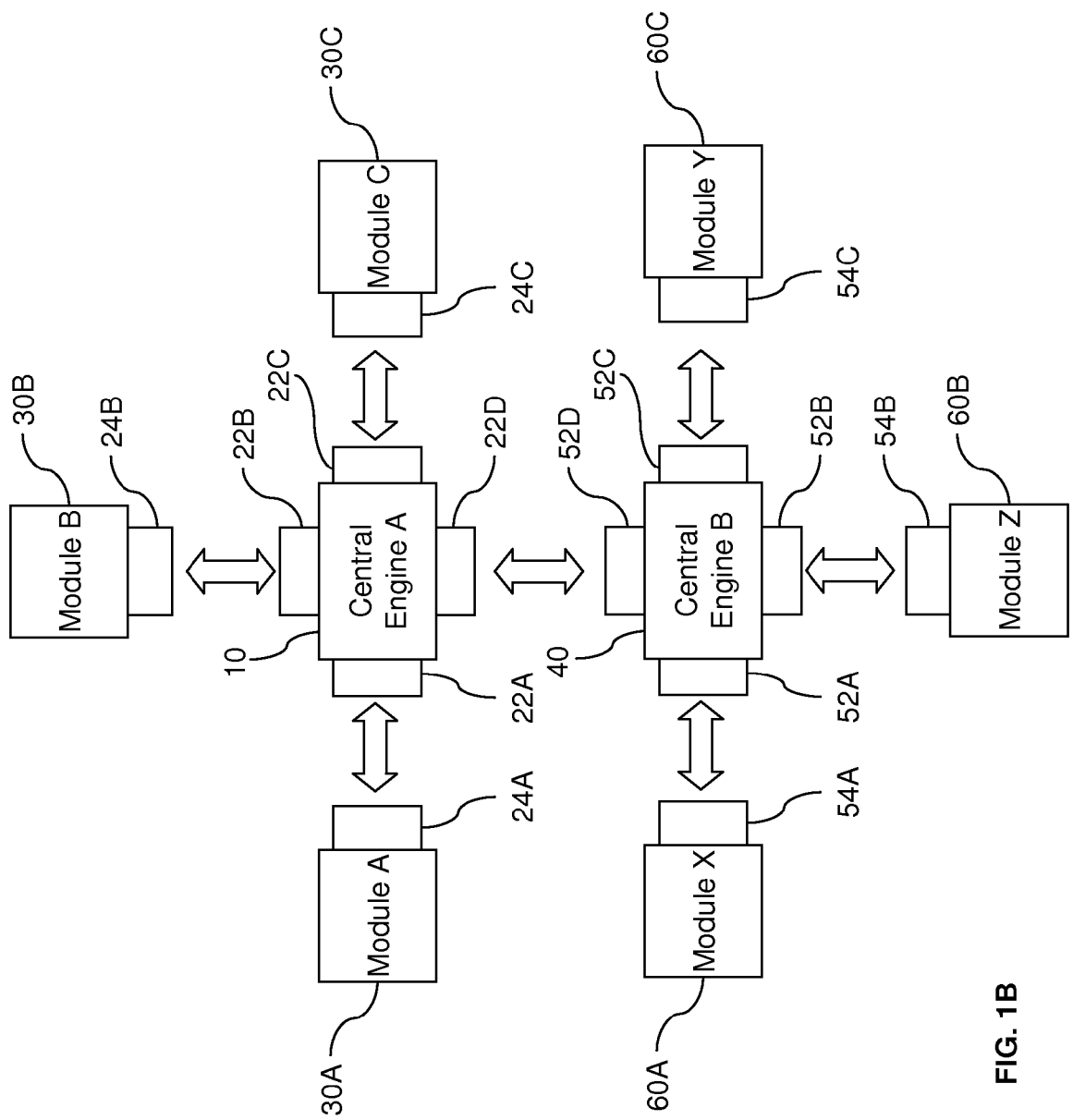
FIG. 1B illustrates a diagram of another architecture according to aspects of the present invention.

Although FIG. 1A illustrates an embodiment with the single central engine 10 connected to modules 30A, 30B, 30C, and 30D, the central engine 10 in some embodiments may also connect to a secondary central engine 40 as illustrated in FIG. 1B. As shown in FIG. 1B, the central engine 10 is connected to modules 30A, 30B, and 30C via corresponding interface elements 22A/24A, 22B/24B, and 22C/24C. Meanwhile, the central engine 40 is connected to modules 60A, 60B, and 60C via corresponding interface elements 52A/54A, 52B/54B, and 52C/54C. As with the modules 30A, 30B, and 30C, the modules 60A, 60B, and 60C may be developed independently of the other modules according to a modular architecture that only requires a single interface with the central engine 40. As further illustrated in FIG. 1B, the central engine 10 may be connected to the central engine 40 via interface elements 22D and 52D. Like the other interface elements, the interface elements 22D and 52D may provide wired, i.e. physical, or wireless communications. In some embodiments, the central engine 10 assumes a host function for the central engine 40. For example, if the central engine 10 connects to the central engine 40 according to universal serial bus (USB) communication protocol, standard USB requires a host-slave relationship between the two systems.

In the embodiment of FIG. 1B, the central engine 10 may access the functionalities provided by the modules 60A, 60B, and 60C, and conversely, the central engine 40 may access the functionalities provided by the modules 30A, 30B, and 30C. Even though the resulting combination may function like a single central engine connected to all six modules 30A, 30B, 30C, 60A, 60B, and 60C, the central engines 10 and 40 may be developed separately. As such, the development of a set of modules can be advantageously organized into separate subsets. For example, medical diagnostic systems may include critical medical devices, such as a blood-glucose meter, as well as other types of devices, such as a heart rate monitor. The critical medical devices may require very rigorous product validation during development and may be subject to government regulations. Meanwhile, the other types of devices may not require the same type or same level of validation. As such, modules involving critical medical devices may have very different timelines and guidelines for product development compared to the other types of health care devices. Thus, in this case, it may be advantageous to organize the modules into two product development groups. In addition, every time a product involving critical medical devices is redeveloped or updated to include new features, government regulations may require revalidation of the product even if the new features may be relatively minor. For example, if a heart rate monitor is added to a central engine that is already connected to a blood-glucose meter, the entire system may have to be revalidated at great cost and effort, even though the new modules is a less critical health care device. However, the central engine connected to the blood-glucose meter can remain unchanged if the central engine already has the capability to connect to a secondary central engine that in turn is connected to the heart rate monitor. In other words, deploying new modules involving other health care devices and other features through the secondary central engine provides a way to expand the overall product without changing the architecture associated with the primary central engine. Moreover, any validation of the architecture associated with the secondary central engine may be conducted without affecting the architecture associated with the primary central engine.

Although an advantage of the architectures described herein is the ease by which new modules can interface with the system and establish communications and data exchange, issues relating to the security of personal medical data have discouraged using highly compatible communication technologies with medical devices, such as personal testing devices that measure and store health data. To address these issues, embodiments according to aspects of the present invention provide functionality that helps to ensure that unauthorized individuals or devices cannot connect with the system and compromise the security of any personal medical information. The central engine 10 may be responsible for providing security measures. Alternatively or additionally, a component or module with special security functions may be employed to promote system security. With such security functionality, particular technologies, such as wireless communication, can be implemented as components of medical diagnostic systems without heightened concern over unauthorized access to personal information.

FIGS. 2A-D illustrate examples of security techniques that may be employed by an architecture according to aspects of the present invention. As shown in FIG. 2A, the central engine 10 may prompt the user for a user ID and password, personal identification number (PIN), or other authentication information, when a module 30 attempts to interface with the central engine 10 or to access data through the system. The module 30 is only allowed connection or data access if the response to the security prompt corresponds with authentication information stored at the system. For example, the module 30 may be a PC executing a data-management program that uploads test data from a blood-glucose meter connected to the central engine 10. When the program attempts to communicate through an interface connection or tries to access data, the user must submit a user ID and password. The authentication information may be entered through a user interface, e.g. a keypad or keyboard, on the PC or the central engine 10. If the module 30 is used frequently to access data through the central engine 10, the user may find it inconvenient to enter authentication information repeatedly. Thus, some embodiments may allow a user to set a time period (from zero to infinity) between authentications from the particular module 30. The central engine 10 records a unique identifier, e.g. device ID, for module 30 to keep track of the time period. For instance, a security prompt may be required if the specified time, e.g. one day, has passed since the last authentication. Alternatively, the user may stop all further security prompts from occurring after the first authentication. In this alternative case, the first authentication acts as a registration with the central engine 10 to permit all future access from the module 30.

As shown in FIG. 2B, a unique identifier, e.g. device ID, for module 30 may be registered with the central engine 10. This unique identifier may be entered by the user or recorded when the authentication process shown in FIG. 2A is completed for the first time. Alternatively, registration of the module 30 may be achieved through an initial, e.g. factory, set-up process. In this alternative case, registration of additional modules may be prohibited after the initial set-up, thereby fixing the number of modules in the system. When the module 30 subsequently attempts to connect or access data, the central engine 10 automatically recognizes the module 30 and permits access.

In the embodiments of FIGS. 2A and 2B, the module 30 is authenticated or registered in a one-way process. In other words, the central engine 10 is not required to be authenticated or registered with the module 30. In contrast, as shown in FIG. 2C, both the central engine 10 and the module 30 are required to be registered with each other. Matching of unique identifiers for the pair is required before any communication takes place between the central engine 10 and the module 30. This pair matching is particularly applicable to wireless communication between two devices. The process prevents intentional unauthorized access, and also prevents interference between two different systems. For example, if a user is in a setting, such as a hospital or clinic, where others are using similar wireless analyte-testing devices, such as blood-glucose meters, pair matching prevents another person's blood-glucose meter from accidentally communicating with the user's diagnostic system and providing the wrong data.

Data security may also be enhanced by using encrypted data during communications, as shown in FIG. 2D. This is also particularly applicable to wireless communications, so that any intercepted data will be unreadable. The data encryption may be achieved by using private encryption keys.

Data security may be further enhanced by ensuring that all data is stored by the central engine 10 within memory in the architecture and is not transferred to any connected modules. Thus, a user may, for example, use a public computer to interface with the system and no data will be transferred to the public computer for others to access.

Figure 3:
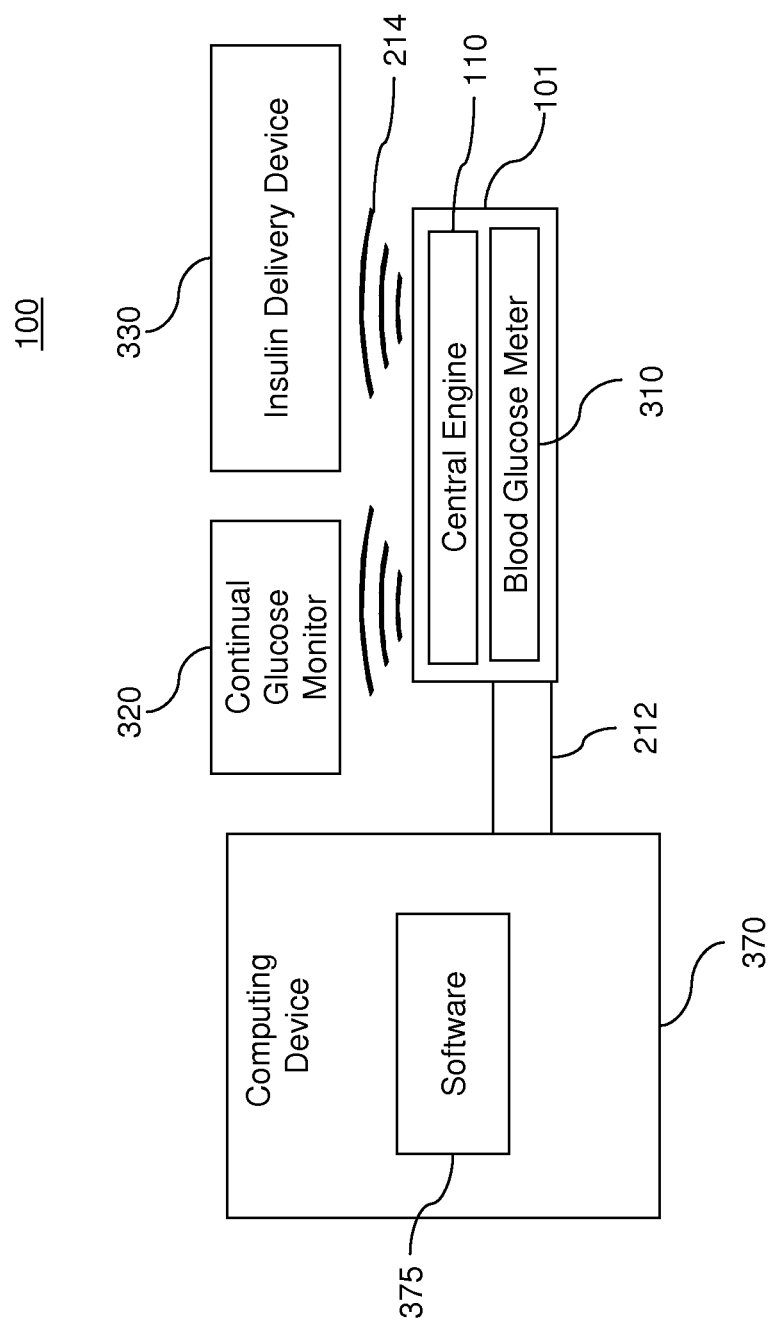
FIG. 3 illustrates an example diabetes-management system employing an architecture according to aspects of the present invention.

FIG. 3 provides a non-limiting example of a diabetes-management system 100 that can be formed from the architecture approach described herein. The diabetes-management system 100 is advantageous to those individuals who are actively involved in monitoring and recording measurements of their blood glucose concentrations and/or other analytes of interest.

As shown in FIG. 3, the diabetes-management system 100 includes a blood-glucose meter (BGM) 310, a continuous glucose monitoring (CGM) module 320, an insulin-delivery device 330, and a computing device 370, which may include diabetes data management software 375. The modules 310, 320, 330, and 370 are combined, as described further below, using the architecture approaches described herein to provide health monitoring and delivery functions for the diabetes-management system 100. In particular, the BGM 310 provides point-in-time measurements of blood-glucose concentrations in blood samples; the CGM module 320 provides continuous measurements of blood-glucose concentration; and the insulin-delivery device 330 delivers insulin to the user.

In addition, the computing device 370 executes the software 375 to receive data from the modules 310, 320, and 330 and provides advanced data processing and management capabilities. The computing device 370 may be selected from a variety of processing devices, such as desktop or laptop personal computers (PCs), handheld or pocket personal computers (HPCs), compatible personal digital assistants (PDAs), and smart cellular phones. The processing devices may employ a variety of operating systems and configurations. For example, if the computing device 370 is a desktop or laptop personal computer, the operating system may be a version of Microsoft® Windows®. Alternatively, if the computing device 370 is a PDA, the operating system may correspond with those of PALM® handhelds from Palm, Inc., or Blackberry® devices from Research in Motion Limited. In general, computing device 370 includes a processor that is capable of receiving and executing any number of programmed instructions.

The data-management software 375 on the computing device 370 may be a collection of programs or computer code that receives and processes data measured by the modules 310 and 320, for example. The software 375 processes and/or displays this input in a manner that is desired by the user. This information may be used by, for example, a user, home care provider (HCP), and/or a physician. The measured data from the modules 310 and 320 may include, for example, the concentration of glucose and/or other analytes in a person's blood or other bodily fluid. Advantageously, the software 375 can provide the advanced displays and data processing that may be required by a user who tests multiple times a day (e.g., about six to about ten times a day). For example, the software 375 may include a product similar to WINGLUCOFACTS® Diabetes Management Software available from Bayer HealthCare LLC (Tarrytown, N.Y.). As such, the software 375 may provide a complete tool kit that receives and stores test results from a blood-glucose measurement system, receives and stores other testing information such as test times and meal markers, tracks test results in an electronic logbook, calculates averages and provides statistical analysis of outlier test results, summarizes and provides feedback on the test results, provides a customizable graphical user interface, displays user-friendly charts and graphs of the test results, tracks test results against user-specific target ranges, provides predictive analysis, and/or sends data to healthcare professionals via fax, email, etc. As described previously, data security is enhanced if the software 375 does not upload data from the modules 310 and 320 to the computing device 370 and the data is always stored within a single central storage device.

Figure 4:
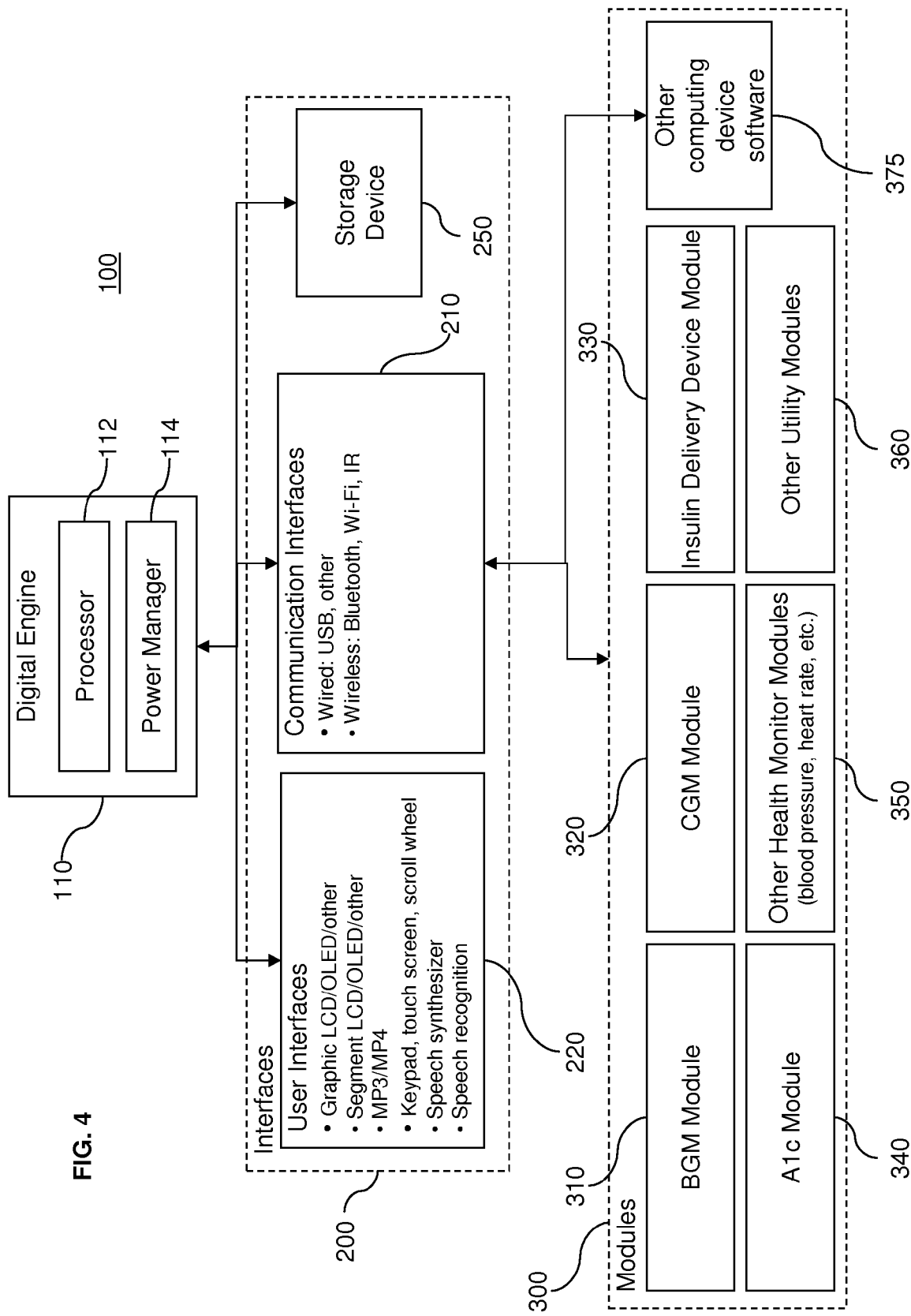
FIG. 4 illustrates another diagram of an architecture according to aspects of the present invention.

As described further below, the use of software or programmed instructions is not limited to the computing device 370. Moreover, the use of embodiments of the present invention are not using the particular modules 310, 320, 330, and 370. FIG. 4 illustrates a broader system diagram with other modules 300. For instance, as FIG. 4 illustrates, an $A1_C$ module 340, which monitors glucose control over time, may also be used in a diabetes-management system. The modules 300 also include other health monitor modules 350, such as blood pressure and heart rate monitors. Indeed, modules 300 may measure and/or record health data that do not require analyte testing, such as temperature measurements, blood pressure measurements, heart rate measurements, breathing measurements for chronic obstructive pulmonary disease (COPD) analysis, weight measurements for analyzing Lasix use, and the like. In further systems, other utility device modules 360 may include training modules, connectivity modules providing further connection to other systems, and other modules that improve or enhance a user's experience with the system. For example, it is contemplated that entertainment or media modules such as game modules or music player modules may be combined with the systems described herein. Providing entertainment features, for example, may encourage patients, particularly young patients, to keep the diagnostic systems with them wherever they go, so that health conditions, such as diabetes, can be monitored regularly. Furthermore, in some systems, the architecture may also employ open source code so that additional custom or specialized modules may be developed by users or third parties for integration with the architecture described herein. Accordingly, an endless variety of modules providing any type of functionality may be employed.

As shown in FIG. 3, the system 100 includes a central engine 110, such as a digital engine, for the architecture and enables the modules 300 to be easily and effectively combined. For example, the central engine 110, the BGM 310, the CGM module 320, and the insulin-delivery device 330 can be effectively combined to create an artificial pancreas. Alternatively, the central engine 110, the BGM 310, and the CGM 320 can be combined to form a CGM with an embedded BGM unit. Or as a further example, the central engine 110, the BGM 310, and the insulin-delivery device 330 can be combined to form a pump controller with an embedded BGM unit.

Referring again to FIG. 4, the central engine 110 may include a processor 112 and a power management element 114. The processor 112 is capable of receiving and executing any number of programmed instructions, and may be a microcontroller, microprocessor, digital signal processor, or the like. The programmed instructions to be executed by the processor 112 may be embedded or may be retrievable from a storage device 250, a connected module 300, or another source such as an Internet website. The processor 112 centrally manages communications with the modules 300. In some cases, the processor 112 may also execute software that handles the operation of some modules 300. Moreover, the processor 112 may give the modules 300 access to common resources or features such as the user interfaces 220 described further below.

Power management element 120 distributes power from a power supply to the processor 112 as well as modules 300 that do not have their own power source. The power management system 114, for example, may be configured to enter a standby mode to minimize power use when the system is idle. Additionally, if a rechargeable battery is employed, the power management system 114 may also handle the recharging of the battery.

As also shown in FIG. 4, the central engine 110 is connected to input/output interfaces 200, which can be divided into two different categories: communication interfaces 210 and user interfaces 220. The communication interfaces 210 govern the exchange of data between the central engine 110 and the modules 300. In general, the communication interfaces 210 can accommodate wired and/or wireless communications. Wired communications include, for example, communications by universal serial bus (USB) connection. Wireless communications include, for example, radio-frequency (RF) links (e.g., a short-range RF telemetry), infrared (IR) links, and/or Wi-Fi. Some known RF technologies, for example, include Bluetooth® wireless technologies, Zigbee, Z-Sense™ technology, FitSense, and BodyLAN™ system. It is understood that other communication technologies, or protocols, may be employed.

Referring again to FIG. 3, a wired, or physical, connection 212 exists between the central engine 110 and the computing device 370 while a wireless connection 214 exists between the central engine 110 and each of the CGM module 320 and the insulin-delivery device 330. It is noted that the BGM 310 is assembled with the central engine 110 in the housing 101. As such, the interface between the central engine 110 and the BGM 310 involves a wired connection (not shown). Indeed, as FIG. 3 illustrates, the modules 300 may be combined in any suitable arrangement in relation to the central engine 110 and to other modules 300. Like the BGM 310, some modules 300 may be assembled with the central engine 110 within the same housing, while other modules 300 may be provided in separate housings and arranged remotely from the central engine 110. It is also contemplated that in addition to other configurations described herein, some modules 300, having the form of circuit components, for example, may be assembled on the same printed circuit board assembly (PCBA) as circuit components for the central engine 110 with a circuit connection providing the interface 210.

Figure 5:
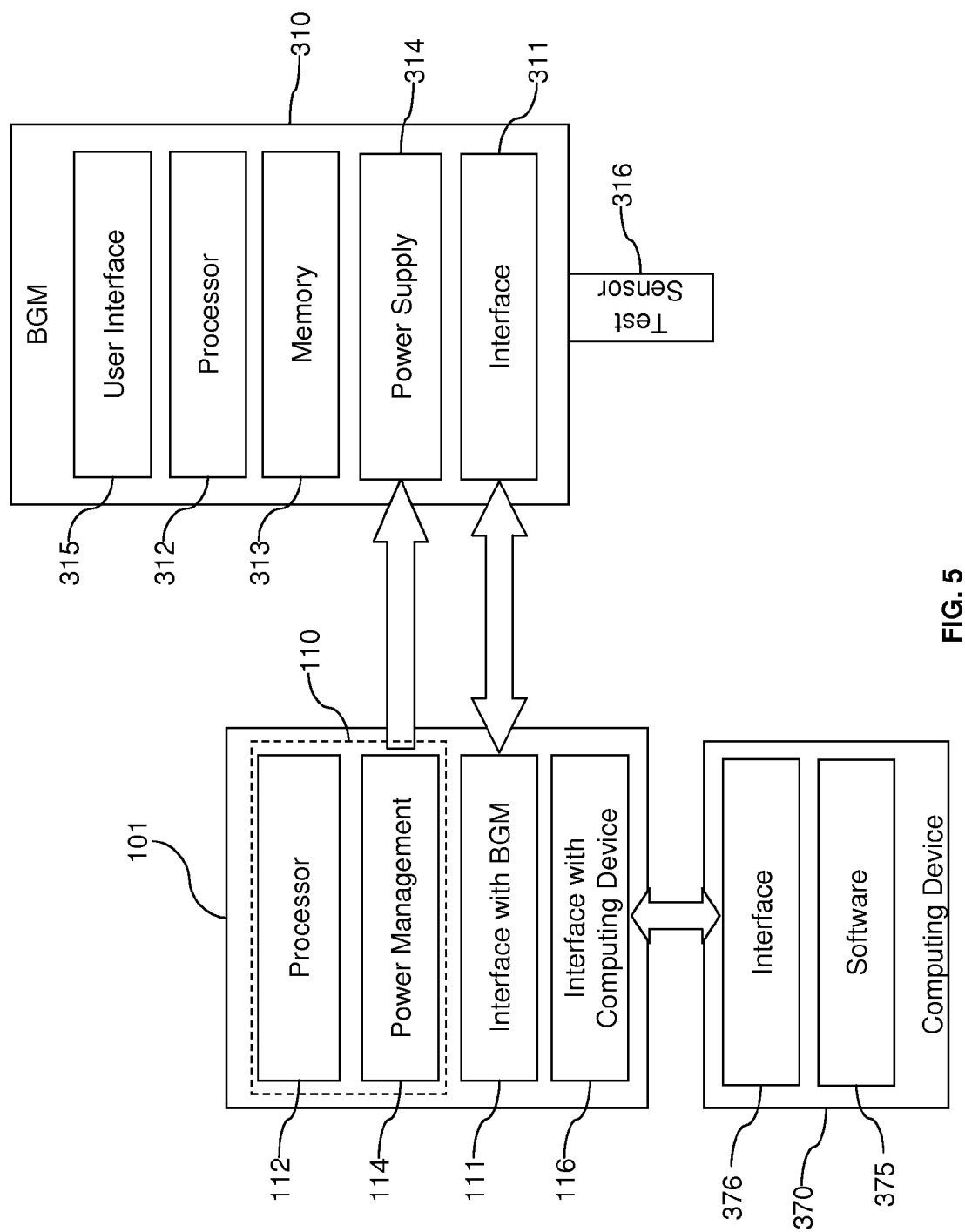
FIG. 5 illustrates an example of a diagnostic system employing an architecture according to aspects of the present invention.

FIG. 5 illustrates a further example of a connection between the central engine 110 and a module 300, namely the BGM 310. Unlike FIG. 3, the BGM 310 of FIG. 5 is not disposed in a housing 101 with the central engine 110, but the description provided with reference to FIG. 5 is equally applicable to the configuration in FIG. 3.

Referring to FIG. 5, the BGM 310 with a test sensor 316 is illustrated. The test sensor 316 is configured to receive a fluid sample which is analyzed using the BGM 310. Analytes that may be analyzed include glucose, lipid profiles (e.g., cholesterol, triglycerides, LDL and HDL), microalbumin, hemoglobin $A1_C$ fructose, lactate, or bilirubin. It is contemplated that other analyte information may be determined (e.g., analyte concentrations). The analytes may be in, for example, a whole blood sample, a blood serum sample, a blood plasma sample, other body fluids like ISF (interstitial fluid) and urine, and non-body fluids.

The test sensor 316 includes a fluid-receiving area for receiving a sample of body fluid. For example, a user may employ a lancet or a lancing device to pierce a finger or other area of the body to produce the blood sample at the skin surface. The user may then collect this blood sample by placing the test sensor 316 into contact with the sample. The fluid-receiving area may contain a reagent which reacts with the sample to indicate the concentration of an analyte in the sample.

The test sensor 316 may be an electrochemical test sensor. An electrochemical test sensor typically includes a plurality of electrodes and a fluid-receiving area that contains an enzyme. The fluid-receiving area includes a reagent for converting an analyte of interest (e.g., glucose) in a fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. In general, the enzyme is selected to react with the desired analyte or analytes to be tested so as to assist in determining an information related to an analyte (e.g. analyte concentration) of a fluid sample. If the concentration of another analyte is to be determined, an appropriate enzyme is selected to react with the analyte.

Alternatively, the test sensor 316 may be an optical test sensor. Optical test sensor systems may use techniques such as, for example, transmission spectroscopy, diffuse reflectance, or fluorescence spectroscopy for measuring the analyte concentration. An indicator reagent system and an analyte in a sample of body fluid are reacted to produce a chromatic reaction, as the reaction between the reagent and analyte causes the sample to change color. The degree of color change is indicative of the analyte concentration in the body fluid.

The color change of the sample is evaluated to measure the absorbance level of the transmitted light.

Some commercially available test sensors that may be used by the embodiments described herein include those that are available commercially from Bayer HealthCare LLC (Tarrytown, N.Y.). These test sensors include, but are not limited to, those used in the Ascensia® CONTOUR® blood glucose monitoring system, the Ascensia® BREEZE® and BREEZE®2 blood glucose monitoring system, and the Ascensia® Elite® and Elite® XL blood glucose monitoring system. It is contemplated that other test sensors, in addition to the ones listed above, may be incorporated into the methods and systems of the present invention.

As illustrated in FIG. 5, the BGM 310 receives and engages the test sensor 316. The BGM 310 includes a reaction-detection system for measuring the concentration of analyte for the sample collected by the test sensor 316. For example, the reaction-detection system may include contacts for the electrodes to detect the electrochemical reaction for an electrochemical test sensor. Alternatively, the reaction-detection system may include an optical detector to detect the chromatic reaction for an optical test sensor. To calculate the actual concentration of analyte from the electrochemical or chromatic reaction measured by the reaction-detection system and to generally control the procedure for testing the sample, the BGM 310 employs at least one processor 312, which may execute programmed instructions according to a measurement algorithm. Data processed by the processor 312 may be stored in a memory 313. Furthermore, the BGM 310 may have a user interface 315 that includes a display, which, for example, may be a liquid-crystal display. Pushbuttons, a scroll wheel, touch screens, or any combination thereof, may also be provided as a part of the user interface 315 to allow a user to interact with the BGM 310. The display typically shows information regarding the test results, the testing procedure and/or information in response to signals input by the user.

Although the BGM 310 can store test results and provide a user interface 315 to display test results, the data-management software 375 on the computing device 400 provides more advanced functionality for managing, processing, and displaying test results and related information. Therefore, the test-related data collected by the BGM 310 can be communicated via the central engine 110 to the computing device 370 for use with the data-management software 375. As shown in FIG. 5, the BGM 310 includes a BGM interface element 311 that enables the BGM 310 to connect with the central engine 110 via the engine interface element 111. Furthermore, the central engine 110 is connected to the engine interface element 116 which in turn is connected to computer interface element 376 of computing device 370. The BGM interface element 311, the computer interface element 376, and the engine interface elements 111 and 116 may employ the interface technologies described above to make the devices compatible and enable the appropriate data connections. For example, engine interface 111 and BGM interface 311 may connect via Bluetooth® wireless, while the engine interface 111 may connect to the computer interface 376 through a connection to a USB port. Thus, it is readily seen that although the BGM 310 and the computing device 370 may not have compatible interfaces, the architecture of FIG. 5 enables data to be exchanged between them. Moreover, it is also readily contemplated that the development of the BGM 310 can be accomplished without regard to direct compatibility with USB interface of the computing device 370.

As discussed previously, the central engine 110 has the power management 114 which may include a power supply that is rechargeable via the connection with the computing device 370 or some other power source. When the central engine 110 and the BGM 310 are connected, a rechargeable battery can be recharged via power management 314.

As described previously, the BGM 310 in FIG. 5 employs at least one processor 312, which may execute programmed instructions. Moreover, the BGM 310 may have a user interface 315, which includes a display to present information to the user, as well as pushbuttons, a scroll wheel, touch screens, or any combination thereof to enable interaction by the user. With such components, the BGM 310 generally controls the whole procedure for testing the sample and calculates the test results. Indeed, the description provided with reference to FIG. 5 generally explains how the test results already calculated by the BGM 310 may be subsequently shared with other modules such as the computing device 370. However, it is contemplated that the processor 112 of the central engine 110 can also provide a wider range of functions. In fact, it is further contemplated that the processing in a health monitoring and delivery system can be distributed among the components, including the central engine 110, in varying manners.

Figure 6:
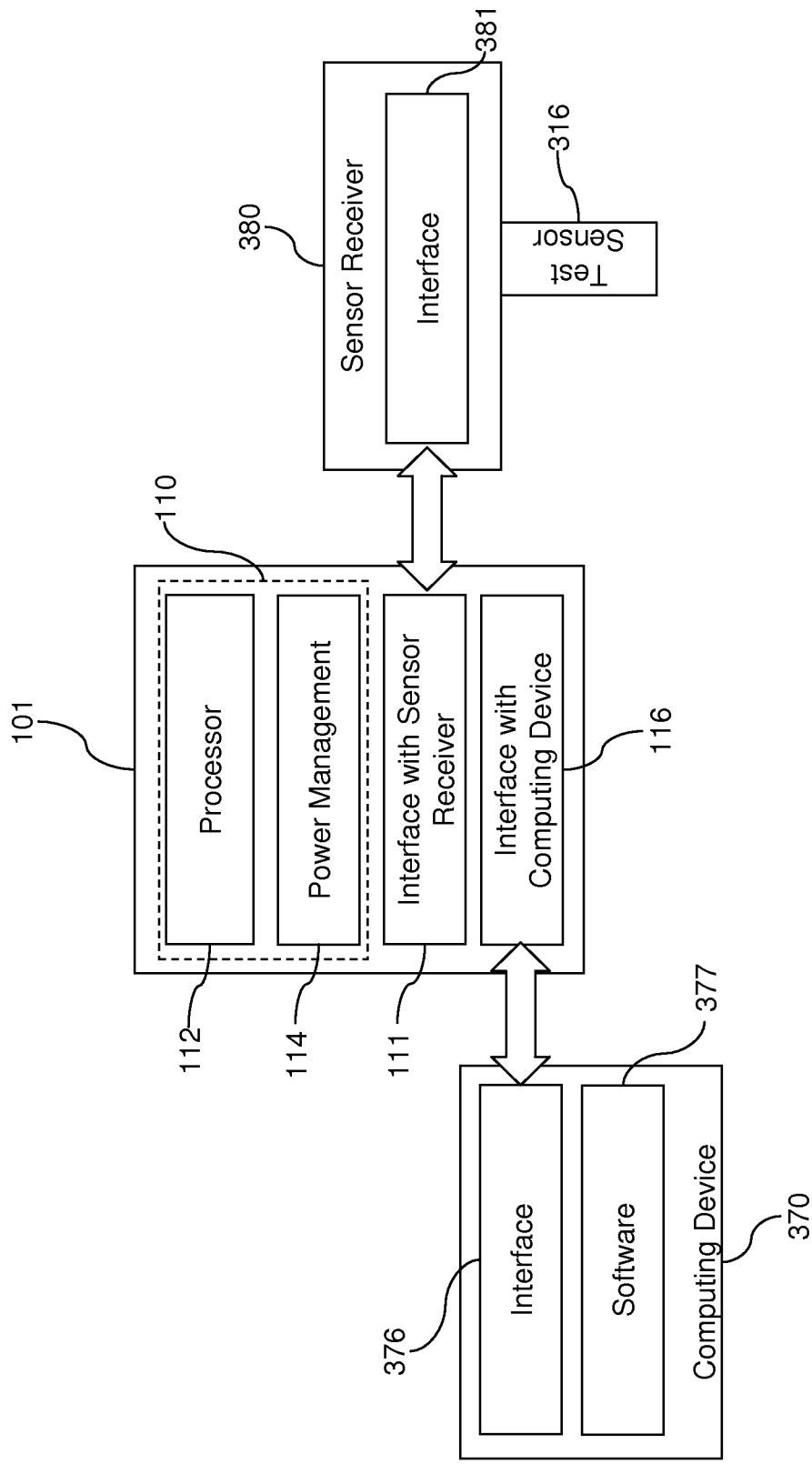
FIG. 6 illustrates another example of a diagnostic system employing an architecture according to aspects of the present invention.

For example, FIG. 6 illustrates a sensor-receiving module 380 that requires other components to handle substantially all of the processing. Like the BGM 310, the sensor-receiving module 380 is configured to receive a test sensor 316. However, the sensor-receiving module 380 does not have a processor to manage the testing procedure or to calculate test results. In addition, the sensor-receiving module 380 has no user interface to communicate with the user. In general, the sensor-receiving module 380 is designed to merely receive a test sensor 316 and to provide an interface element 381 for physical connection to the rest of the diagnostic system. As a result, analysis of the test sample on the test sensor 316 is only possible when the sensor-receiving module 380 connects with a device that has a processor to analyze the sample via the interface element 381.

As shown in FIG. 6, the interface element 381 of the sensor-receiving module 380 is connected to the interface element 111, which in turn is connected to the digital sensor 110. It is noted that the connection between the sensor-receiving module 380 and the central engine 110 may require a host function, such as the USB host function, to be employed by the central engine 110. In one embodiment, the digital sensor 110 is also connected to the interface element 376 of the computing device 370. The interfaces between the sensor-receiving module 380, the central engine 110, and the computing device 370 may employ any of the interface technologies, such as USB or Bluetooth® technology, described above. Accordingly, the computing device 370 can execute software 377 to control the procedure for testing a sample and calculating the test results in a manner similar to the processor 312 on BGM 310 in FIG. 5. In operation, the sensor-receiving module 380, the central engine 110, and the computing device 370 are connected as shown in FIG. 6. The test sensor 316 is used to collect a fluid sample, such as a blood sample. If, for example, the test sensor 316 is an electrochemical test sensor, the sensor-receiving module 380 system may include electrical contacts to receive the electrical signal from the electrochemical reaction that occurs between the sample and the reagent on the test sensor 316. The connection between the sensor-receiving element 380 and the central engine 110 is connected to the circuit containing the electrical sensors so that the central engine 110 receives the electrical signal from the electrochemical reaction. This signal can then be passed to the computing device 370 to process the signal and determine the test results using a measurement algorithm. The user interface on the computing device 370 can be used to display the test results or to receive instructions from the user.

It is understood that other techniques may be employed to communicate a signal from the sensor-receiving module 380. For example, a test sensor 316 may be an optical test sensor and the sensor-receiving system 380 may include an optical detector to detect a chromatic reaction. If the sensor-receiving module 380 requires any power to receive or process a signal from the test sensor 316, the power can be drawn through its connection with the central engine 110.

Figure 7:
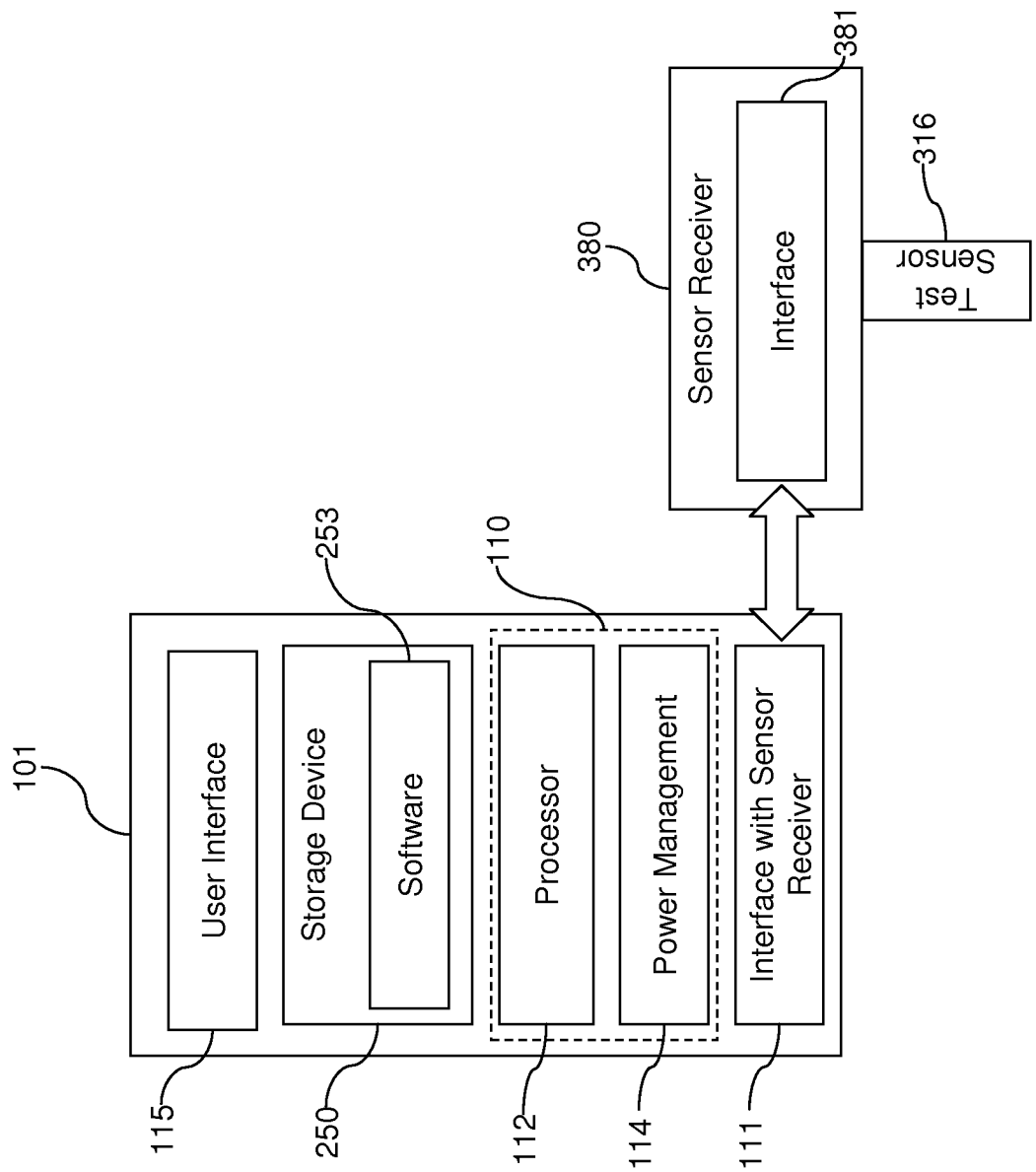
FIG. 7 illustrates yet another example of a diagnostic system employing an architecture according to aspects of the present invention.

Alternatively, in another embodiment, the computing device 370 is not employed in the system, so that the sensor-receiving module 380 is only connected to the central engine 110 as shown in FIG. 7. As such, the test result calculations are completed by the processor 112 of the central engine 110 and the test results are displayed on a user interface connected to the central engine 110. As shown in FIG. 7, a user interface 115 may be incorporated into the housing 101.

The measurement software 253 for controlling the test process and determining the results may be available through the storage device 250 as illustrated in FIG. 7. As illustrated in FIG. 4, the storage device 250 corresponds with another type of input/output interface 200. The storage device 250 may be a flash memory device, such as a universal serial bus (USB) flash drive or a memory card. USB flash drives are also known as thumb drives, handy drives, flash sticks, or jump drives. Memory cards may have a variety of formats, including PC Card (PCMCIA), CompactFlash (CF), SmartMedia (SM/SMC), Memory Stick (MS), Multimedia Card (MMC), Secure Digital Card (SD), xD-Picture Card (xD), Intelligent Stick (iStick), ExpressCard, or some variation thereof. Flash memory devices may employ non-volatile memory so that the software associated with the measurement software 253 may be retained in the storage device 250 even when the storage device 250 receives no power. In some embodiments, the memory in the storage device 250 may include execute-in-place (XIP) memory, such as NOR flash memory, so that the measurement software 253 stored on the memory can be executed directly. It is also contemplated that the storage device 250 may employ other storage media, such as floppy disk or optical disc (CD, DVD, Blu-ray disc).

The storage device 250 may be assembled with the central engine 110 in the housing 101, as shown in FIG. 7, or it may be connected to the central engine 110 in a manner similar to an external module (e.g., module 300). Particularly in the latter case, the storage device 250 may interface with a communications interface 210 and connect to the central engine 110. The interface enables data communications between the storage device 250 and the central engine 110 and permits the measurement software 253, or any other software, to be used with central engine 110. In particular, the storage device 250 has an interface element that is compatible with an interface element 210. In some embodiments, the storage-device interface element physically engages the interface element 210 to form a serial hardware interface. For example, the storage device 250 may be a USB flash drive, and the storage-device interface element may be a USB connector that is received into a USB port, which acts as the communications interface element 210 for the central engine 110.

As a further example, the storage device 250 may be a Secure Digital (SD) memory card with a series of contacts that act as the interface element, and the communication interface 210 may be an expansion slot that receives the contacts of the memory card. In this example, the central engine 110 and the storage device 200 may comply with SDIO (Secure Digital Input Output) interface specifications. It is contemplated that other memory card formats having different interface specifications may be employed. However, having an SDIO is advantageous because many hosts such as PDAs, HPCs and smart cellular phones include an expansion slot that is SDIO compatible.

As the central engine 110 in FIG. 7 is filling the role of the computing device 370 in the example of FIG. 6, higher-powered processing devices may be required. For example, some embodiments may employ handheld or pocket personal computers (HPCs), compatible personal digital assistants (PDAs), or smart cellular phones. As discussed above, these processing devices may employ a variety of operating systems and configurations. For example, if the computing device 370 is a PDA, the operating system may correspond with those of PALM® handhelds from Palm, Inc., or Blackberry® devices from Research in Motion Limited. Advantageously, PALM® handhelds and Blackberry® devices provide a portable device with enough processing power to reliably execute advanced data management software for results collected from the sensor-receiving module 380. Moreover, such devices provide rich user interfaces that provide advanced graphical display capabilities. In addition, because these handheld devices connect to external networks, such as the Internet, new software or software upgrades/patches can be readily installed. Furthermore, the connection to the telecommunications network enables test results to be easily transmitted to doctors and other healthcare professionals for monitoring or evaluation. Because many consumers already carry these or similar devices, many users of a diagnostics system, such as a diabetes-management system, would conveniently incorporate the system in devices they already own and carry regularly.

Because embodiments may employ many different types of modules 300 that may be situated on different types of hardware, the communication interfaces 210 generally have to accommodate more than one type of communication technology, or protocol. However, to minimize the number of communication interfaces 210 while providing the widest range of compatibility between the central engine 110 and the various modules 300, the communication interfaces 210 can employ widely-used and standardized interface technologies, such as USB or Bluetooth® technology. Preferably, the communication interfaces 210 employ technologies that minimize the amount of configuration required to establish communication between a module 300 and the central engine 110. Indeed, some communication technologies, such as USB connectivity, provide plug-n-play (PnP) capability. In these embodiments, the module 300 is physically connected, for example, through a conventional USB port. Then in response, the central engine 110 immediately recognizes the module 300 and establishes immediate communication with the module 300.

The communication interfaces 210 not only provide communication between modules 300, but they also enable secure communication with external networks. As such, embodiments may employ a connection to an external network to download updates, upgrades, or additions to the software in the central engine and/or the modules 300 when the product is out in the field. In other words, the embodiments may provide field upgradeable software functions. Advantageously, embodiments allow the user to update any software/firmware in the integrated system, e.g., software for the central engine 110 and/or the modules 300, by using program files provided by, or purchased from, the manufacturer or an authorized third party. Existing system software can be updated or patched with newer versions, or new software may be added to the system, without requiring the user to contact the manufacturer or third party for direct assistance. The new software allows the user to customize and/or expand the functionality of the system. In some cases, a product may be essentially converted to a new product. Field upgrades make the latest product features available to users who have already purchased a product. Moreover, field upgrades making existing product compatible with other newly released accessories or devices. For example, in a diabetes-management system, if the BGM 310 uses a test sensor to test blood for blood glucose concentration, and the BGM manufacturer develops a new test sensor that improves accuracy or test time, embodiments would allow the user to upgrade the firmware in the device so that the BGM 310 is capable of reading the new test sensor.

The central engine may manage aspects of the field upgrade validation in combination with a download engine. The download engine, described further below, can receive system components from a server, e.g., the field upgrade server, the external network via a communication interface and deliver the system components for validation and deployment. Additionally or alternatively, the server on the external network can manage aspects of the field upgrade process.

In addition, due to the important medical functions associated with the modules 300, embodiments employ validation procedures before employing the new software or configuration information to ensure that any field upgrade does not corrupt the data or the software stored by the product and that the product continues to operate as expected. For example, check-sum routines may be employed to confirm that data or software has been successfully downloaded in its entirety. For example, the central engine 110 may validate downloads according to an associated data update file (DUF) or other component that ensures that the software has been successfully downloaded. For additional data security, the field upgrade process may employ data encryption/decryption.

In an example embodiment illustrated in FIG. 9, once a connection is established with a field upgrade server in an appropriate external network (act 502), an available field upgrade is identified for an existing system component, e.g., new software or configuration information, (act 504). The connection to the server may be triggered automatically when a connection to the network may be established, or a user may manually initiate communication with the field upgrade server. To identify an available field upgrade, the central engine or the server may employ a version management program to determine which system components in the architecture are compatible with, and can be replaced by, newer or different versions stored on the field upgrade server. The new system component is then downloaded from the field upgrade server to a memory, i.e., data storage area, that is separate from the memory area storing the existing system component. An area of memory may be specifically dedicated for field upgrade operations. In other words, the existing system component is retained, rather than deleted or written over at least until validation is complete. The new system component is validated with a system check (act 508), and if the download has been successful and the system operates properly, the new system component is deployed for regular system operation. Thus, if the field upgrade fails, the previous version of the system component is still available and provides a recovery or restore option. The new system component is removed with a failed field upgrade. In some embodiments, the new version may replace the previous version in memory after the new version is validated. In other embodiments, the one or more previous versions are retained even after validation and users may have the option to restore one or more previous versions of a system component if an older version is preferred.

Figure 8:
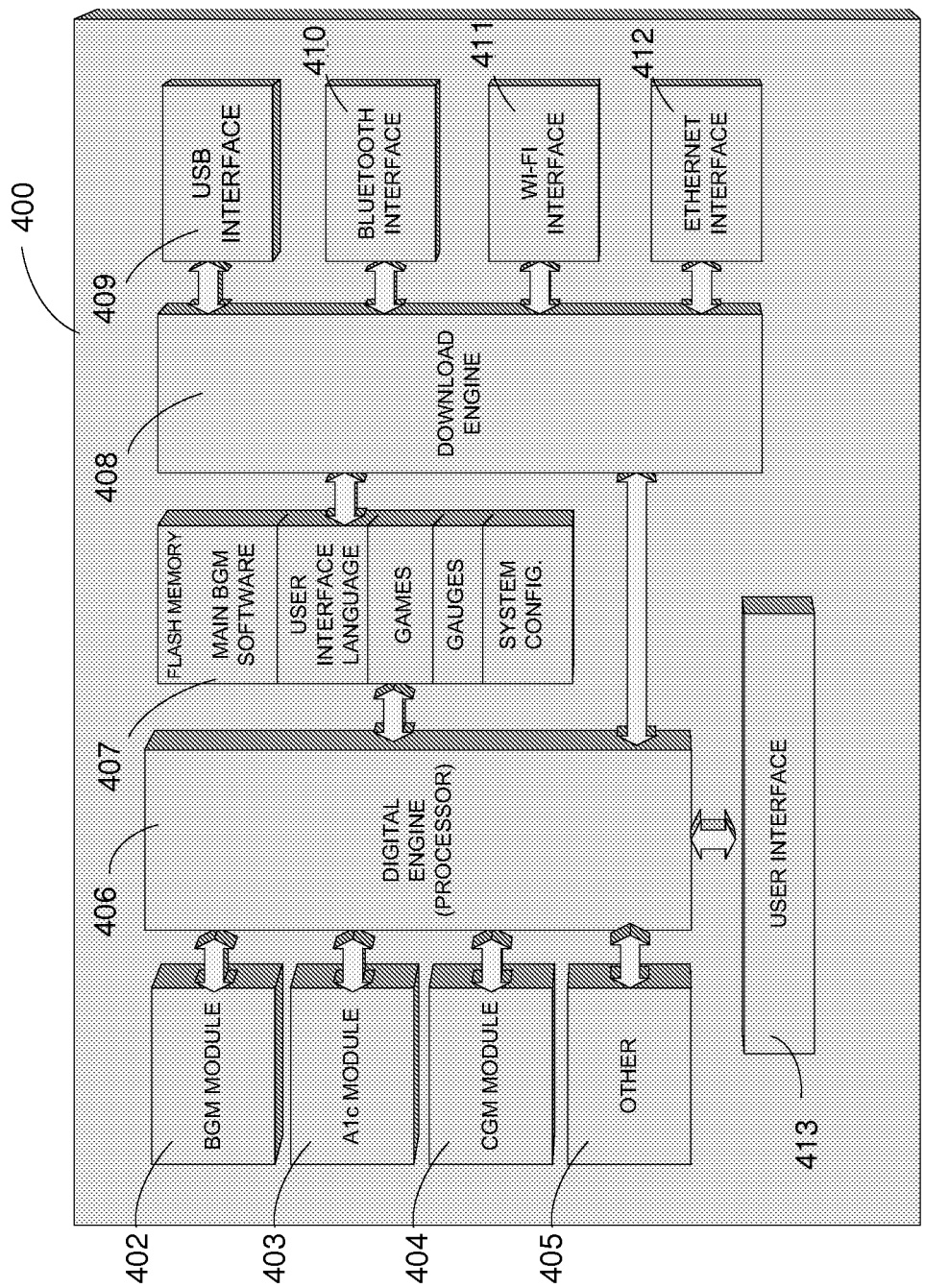
FIG. 8 illustrates a field-upgradeable architecture according to aspects of the present invention.

An example embodiment is described with reference to FIG. 8. In the embodiment of FIG. 8. the diabetes-management system 400 may include modules 402, 403, 404, and 405 which collect fluid samples. The digital engine 406 controls each module, user interface 413, memory 407, and the download engine 408. Download engine 408 provides an interface between one of the communication modules, digital engine 406, and memory 407. The communications modules may include USB interface 409 which provides, for example, communication between a computing device USB port and the system 401. The communication module may also include a Bluetooth interface 410 which provides wireless communication between the system 400 and a computing device, cell phone, and/or other devices capable of communicating with the system 400. Furthermore, a Wi-Fi interface 411 provides communication between a wireless network and the system 400. Additionally, the Ethernet interface 411 provides communication between a local area network and the system 400. Each communication module can be used to upgrade/update the meter's software in the field upon the user's direction. The following features may also be downloaded per user request: new firmware for new functions; new firmware to update the behavior of current system functions; user interface language; screen updates and customization; games and other standalone applications; gauges; and other software or configuration settings/updates.

For example, the user interface may communicate in many languages, but all the data required for those languages does not have to be stored locally, as users may download language files as required to customize the operation of their systems. In addition, users can customize the appearance of the user interface display by installing custom pictures to display on the screen or by downloading display layouts made available by a manufacturer or an authorized third party. Furthermore, users can customize the behavior of the system by installing standalone applications (such as games) that can run on the system processor and be played when the system 400 is not being used to analyze body fluids. Users can also customize system behavior by installing software that changes the way body fluid analysis results are displayed, as results may be presented as digital readouts, simulated analog gauges, qualitative feedback, etc.

Referring again to FIG. 4, the input/output interfaces 200 also include user interfaces 220, which generally allow the modules 300 to display information, such as test results, to the user. The modules 300 may transmit such information to the central engine 110 via communication interfaces 210, and the central engine 110 may in turn present the information on the display interfaces 220. Although centralized handling of communications may be preferred, the modules 300, in some cases, may interface directly with the display interfaces 220. As shown in FIG. 2, the display interfaces may include graphic liquid crystal display (LCD) or organic light-emitting diode (OLED), segment LCD or OLED, MP4 playback, or the like.

In addition, the input/output interfaces 200 may allow information to be communicated to and from the user via audio signals. For example, the input/output interfaces 200 may include a speech synthesizer, MP3 playback, or the like, for communicating audio information to a user. Additionally, the input/output interfaces 200 may also include a speech recognition mechanism to receive audio information from a user.

Furthermore, the user interfaces 200 may allow the user to input information or instructions into the system. For example, the user may be required to respond to simple prompts or make menu selections to guide one of the modules 300 during operation. Or as a further example, the user may want to enter instructions to retrieve information, such as test results, and to present the information on the display interfaces 220. Mechanisms for providing input, for example, may include a keypad, a touch screen, a thumb wheel, or the like.

As shown in FIG. 7, a user interface 115 may be incorporated into the housing 101 in which the central engine 110 and corresponding communication interfaces 210 are assembled. As such, the housing 101 may form a portable device 101 for a health monitoring and delivery system. As discussed previously with reference to FIG. 3, some modules 300, such as the BGM 310, may be incorporated into the device, while other modules, such as CGM 320 and the insulin delivery module 330, may be externally connected to the portable device 101 through the communication interfaces 210. The modules 300 connected to the digital engine 310 have access to the interface Systems employing the architecture support various types of electronic networks and communications. Modules 300 may be employed, for example, to provide cellular activity. Other embodiments, alternatively or additionally, may employ global positioning system (GPS) technology, which has become widely accessible to civilian applications such as road navigation, people tracking, and timing services. With the technology becoming more and more mature, the cost of integrating this technology into consumer products and medical device has been significantly reduced. GPS receiver chipsets are currently available on market and can be easily integrated with consumer or medical device to provide information on device location, velocity and Universal time. As such, GPS may be provided to enhance the functionality of a system employing architecture to form an integrated system for monitoring a health condition and/or delivering a medication.

With GPS, a diabetes-management system, for example, can provide additional information associated with glucose tests. Accurate timestamps and locations can be associated with readings. The erroneous timestamps generated by conventional meters have been the source of confusion and difficulty when readings from multiple meters are downloaded and merged into one database file, or uploaded to computers or web servers that do not have their local time in sync with the meters. Patient movement and exercise can be tracked automatically, facilitating patient logging effort tremendously. The data may include distance and speed. This information can be used for patient daily activity planning for exercise, diet, medication and blood glucose test frequency, etc. It also enables comprehensive analysis of correlation between reading patterns and daily activities Furthermore, patients can be located in emergencies.

The additional timing, location and physical activity information obtained with GPS, combined with logged diet, medication information, can assist the diabetes-management system to make more accurate predictions on patients' daily blood glucose patterns. The diabetes-management system can make real-time daily activity recommendations that will help them to control their blood glucose levels in the prescribed range. The system can then remind patients to take the right number of tests daily at the right moments.

Accordingly, GPS may be employed to synchronize a system's device's real time clock (RTC) to UMT with high precision so that glucose readings can be associated with correct timestamp. As power for the GPS functionality may be a consideration, the GPS receiver may only need to be activated once a day or a week depending on the device crystal quality. Assuming that each time the GPS consumes 0.175 mAhr power (calculated based on Xemics XE1600 receiver using Trimble chipsets), and the device takes a GPS measurement once a day, 63.9 mAhr is consumed in a year for the GPS related calculation which is roughly about 10-20% of a regular cell phone battery capacity.

As discussed previously, some portable embodiments of an integrated monitoring/delivery system may connect with a computing device 370 for advanced data management. This situation provides the opportunity for applying the NAVSYS GPS recorder model (TrackTag) to the portable device to track patient movement and activity. Because a GPS recorder simply takes snapshots of satellite signals without processing them, a significant amount of power can be saved. Assume the device takes a GPS snapshot once every 150 sec, then in one year this GPS recorder only consumes about 280 mAhr, which is roughly about <50% of a regular cell phone battery capacity. If the device can stop taking snapshots at night then further energy can be preserved. The trade off in using the TrackTag approach is the required amount of on-device memory required. Every snapshot takes about 15 kbyte, so at the above snapshot rate, there will be about 200,000 snapshot per year which requires about 3 Gbyte memory. Of course, once GPS data is downloaded from the device to computer and processed, the device memory can be freed up and reused. It seems that one Gbyte memory may support 4 months of location tracking for the portable device. Using modern flash memory technology, one Gbyte device memory can be easily accommodated.

The GPS functionality may be a built-in central function. In a more modular example, however, the GPS functionality may be provided by a connected module, i.e. a detachable GPS receiver. Indeed, if the GPS receiver module has its own memory to store time and position information, then the GPS may not need to be connected all the time with the DM device. The GPS receiver may be connected with the system once a day or one every few days depending on how often the device clock needs to be synchronized and also on the availability of GPS receiver memory. Advantageously, the use of a detachable GPS receiver module minimized the impact on hardware/software design of the central engine 110 and other aspects of the system. Moreover, power management is facilitated.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

What is claimed is:

1. A system for managing healthcare data, comprising:
mother circuit including a processor and a mother circuit memory area storing a first updatable software;
a first daughter circuit interfacing with the mother circuit, the first daughter circuit including a first daughter circuit memory area storing updatable software that provides a healthcare function;
a second daughter circuit interfacing with the mother circuit and being communicatively isolated from the first daughter circuit thereby enhancing the integrity of the healthcare function provided by the first updatable software, the second daughter circuit including a second daughter circuit memory area storing a third updatable software that provides a second function;
one or more communication interfaces providing a connection to a remote server, the remote server storing one or more program components;

a download engine receiving the one or more program components from the remote server via the one or more communication interfaces, the one or more program components for replacing
  (i) an older version of the first updatable software running on the mother circuit with an updated version of the first updatable software,
  (ii) an older version of the third updatable software running on the second daughter circuit with an updated version of the third updatable software, or
  (iii) both (i) and (ii); and
a restore component that restores the older version of the first updatable software or the older version of the third updatable software when a validation component determines that the updated version of the first updatable software or the updated version of the third updatable software operates incorrectly or has not been downloaded properly, thereby ensuring that the system, including the healthcare function and the second function, continues to operate as expected.

2. The system of claim 1, further comprising a version management component that determines whether the one or more program components is compatible with the mother circuit, the first daughter circuit, or the second daughter circuit before the download engine receives the one or more program components.

3. The system of claim 1, wherein the updated version of the third updatable software is downloaded to a third daughter circuit memory area contained in the second daughter circuit that is separate from the second daughter circuit memory area storing the older version of the third updatable software such that the older version of the third updatable software remains available to be restored.

4. The system of claim 1, wherein the one or more program components provides a patch for software running on the first daughter circuit, the second daughter circuit, or both.

5. The system of claim 1, wherein the one or more program components provides a new function to be executed by the first daughter circuit, the second daughter circuit, or both.

6. The system of claim 1, wherein the one or more program components includes configuration information for software running on the first daughter circuit, the second daughter circuit, or both.

7. The system of claim 1, wherein the download engine is manually triggered by a user to receive and deliver the one or more program components.

8. The system of claim 1, wherein the download engine is automatically triggered to identify the one or more program components when communication to the remote server can be established.

9. The system of claim 1, wherein the one or more interfaces include at least one of a USB interface, a radio frequency (RF) interface, a Wi-Fi interface, and an Ethernet interface.

10. The system of claim 1, wherein when communication to the remote server is established when the download engine is in range of a wireless network.

11. The system of claim 1, further comprising a data validation component configured to validate the one or more program components before the one or more program components is deployed.

12. The system of claim 11, wherein the data validation component determines whether the one or more program components are not corrupted.

13. The system of claim 11, wherein the data validation component determines, with a check-sum routine, whether the one or more program components has been completely transferred from the remote server via the download engine.

14. The system of claim 11, wherein the one or more program components are removed if the data validation determines that the one or more program components are corrupted.

15. The system of claim 1, wherein the second function is different than the healthcare function provided by the second updatable software.

16. The system of claim 1, wherein the second function is a healthcare function.

17. The system of claim 1, wherein the one or more program components are further for replacing an older version of the second updatable software running on the first daughter circuit with an updated version of the second updatable software.

* * * * *

UNITED STATES PATENT AND TRADEMARK OFFICE
CERTIFICATE OF CORRECTION

| | |
|---|---|
| PATENT NO. | : 8,978,026 B2 |
| APPLICATION NO. | : 12/129570 |
| DATED | : March 10, 2015 |
| INVENTOR(S) | : Steven Charlton et al. |

It is certified that error appears in the above-identified patent and that said Letters Patent is hereby corrected as shown below:

IN THE CLAIMS

In Column 18, Line 52, in Claim 1, delete "mother" and insert -- a mother --, therefor.
In Column 18, Line 56, in Claim 1, delete "storing updatable" and insert -- storing a second updatable --, therefor.

Signed and Sealed this
Seventeenth Day of November, 2015

Michelle K. Lee
*Director of the United States Patent and Trademark Office*